US007803566B2

(12) United States Patent
Terajima et al.

(10) Patent No.: US 7,803,566 B2
(45) **Date of Patent: *Sep. 28, 2010**

(54) IDENTIFICATION OF GENE SEQUENCES AND PROTEINS INVOLVED IN VACCINIA VIRUS DOMINANT T CELL EPITOPES

(75) Inventors: Masanori Terajima, Holden, MA (US); John Cruz, Shrewsbury, MA (US); Francis A. Ennis, Shrewsbury, MA (US)

(73) Assignee: The University of Massachusetts, Boston, MA (US)

(*) Notice: Subject to any disclaimer, the term of this patent is extended or adjusted under 35 U.S.C. 154(b) by 0 days.

This patent is subject to a terminal disclaimer.

(21) Appl. No.: 11/731,784

(22) Filed: Mar. 30, 2007

(65) Prior Publication Data

US 2007/0298046 A1 Dec. 27, 2007

Related U.S. Application Data

(63) Continuation of application No. 10/764,985, filed on Jan. 26, 2004, now Pat. No. 7,217,526.

(60) Provisional application No. 60/442,846, filed on Jan. 24, 2003.

(51) Int. Cl.
*G01N 33/53* (2006.01)
*C07K 5/00* (2006.01)

(52) U.S. Cl. .......................... 435/7.24; 435/41; 435/42; 435/2; 435/3; 530/300; 530/328

(58) Field of Classification Search ....................... None
See application file for complete search history.

(56) References Cited

U.S. PATENT DOCUMENTS

| | | | |
|---|---|---|---|
| 4,603,112 | A | 7/1986 | Paoletti et al. |
| 5,674,502 | A | 10/1997 | Ennis |
| 5,766,601 | A | 6/1998 | Ennis |
| 5,882,650 | A | 3/1999 | Ennis |
| 6,232,448 | B1 | 5/2001 | Yoshikubo et al. |
| 6,627,407 | B2 | 9/2003 | Ennis |
| 6,962,790 | B1 | 11/2005 | Ennis |
| 7,026,443 | B1 | 4/2006 | Sette et al. |
| 7,217,526 | B2 | 5/2007 | Terajima et al. |
| 2004/0132132 | A1 | 7/2004 | Sahin et al. |
| 2005/0129703 | A1 | 6/2005 | Ennis et al. |

FOREIGN PATENT DOCUMENTS

| | | | |
|---|---|---|---|
| EP | 1 398 380 | A1 | 3/2004 |
| WO | WO 9/515764 | A1 * | 6/1995 |
| WO | WO 95/24925 | | 9/1995 |
| WO | WO 96/03144 | A1 | 2/1996 |
| WO | WO 97/45444 | | 12/1997 |
| WO | WO 9/803192 | A1 * | 1/1998 |
| WO | WO 99/02550 | | 1/1999 |
| WO | WO 00/24778 | A1 | 5/2000 |
| WO | WO 02/068682 | A2 | 9/2002 |
| WO | WO 2004/024756 | A2 | 3/2004 |
| WO | WO 2004/067032 | A2 | 8/2004 |
| WO | WO 2006/076003 | A2 | 7/2006 |

OTHER PUBLICATIONS

Colman, P.M., "Effects of Amino Acid Sequence Changes on Antibody-Antigen Interactions," *Res. Immunol.*, 145: 33-36 (1994).
Rudikoff, S., et al., "Single Amino Acid Substitution Altering Antigen-Binding Specificity," *Proc. Natl. Acad. Sci. USA*, 79: 1979-1983 (1982).

Drexler, I., et al., "Identification of Vaccinia Virus Epitope-Specific HLA-A*0201-Restricted T Cells and Comparative Analysis of Smallpox Vaccines," *Proc. Natl. Acad. Sci. USA 100*(1):217-222 (2003).

Terajima, M., et al., "Quantitation of $CD8^+$ T Cell Responses to Newly Identified HLA-A*0201-Restricted T Cell Epitopes Conserved Among Vaccinia and Variola (Smallpox) Viruses," *J. Exp. Med. 197*(7):927-932 (2003).

Ramirez, J.C., et al., "Biology of Attenuated Modified Vaccinia Virus Ankara Recombinant Vector in Mice: Virus Fate and Activation of B- and T-Cell Immune Responses in Comparison With the Western Reserve Strain and Advantages as a Vaccine," *J. Virol. 74*(2):923-933 (Jan. 2000).

Gen Bank Acc. No. M35027 "Vaccinia Virus, Complete Genome," (1990, updated 2000).

Wagner, C., et al., "Identification of an HLA-A*02 Restricted Immunogenic Peptide Derived from the Cancer Testis Antigen HOM-MEL-40/SSX2," *Cancer Immunity 3*:18 (2003).

Oseroff, C., et al., "HLA Class I-restricted Responses to Vaccinia Recognize a Broad Array of Proteins Mainly Involved in Virulence and Viral Gene Regulation," *Proc. Natl. Acad. Sci. USA 102*(39):13980-13985 (2005).

Carroll, M.W., et al., "Highly Attenuated Modified Vaccinia Virus Ankara (MVA) as an Effective Recombinant Vector: a Murine Tumor Model," *Vaccine 15*(4):387-394 (1997).

Carroll, M.W., and Moss, B., "Poxviruses as Expression Vectors," *Curr. Opin. Biotechnol. 8*(5):573-577 (1997).

DeLisi, C., et al., "T-cell Antigenic Sites Tend to be Amphipathic Structures," *Proc. Natl. Acad. Sci. USA 82*:7048-7052 (1985).

Bixler, Jr., G.S., and Atassi, M.Z., "T Cell Recognition of Myoglobin: Localization of the Sites Stimulating T Cell Proliferative Responses by Synthetic Overlapping Peptides Encompassing the Entire Molecule," *J. Immunogenet. 11*(5-6):339-353 (1984).

(Continued)

*Primary Examiner*—Patrick Nolan
*Assistant Examiner*—Bao Qun Li
(74) *Attorney, Agent, or Firm*—Hamilton, Brook, Smith & Reynolds, P.C.

(57) ABSTRACT

The present invention relates to the identification of gene sequences and proteins involved in vaccinia virus dominant T cell epitopes. Two vaccinia virus $CD8^+$ T cell epitopes restricted by the most common human MHC class I allele, HLA-A0201 have been identified. Both epitopes are highly conserved in vaccinia and variola viruses. The induction of the T cell responses following primary vaccination is demonstrated by the kinetics of epitope specific $CD8^+$ T cells in 3 HLA-A0201 individuals. This information will be useful for the design and analyses of the immunogenicity of experimental vaccinia vaccines, and for basic studies of human T cell memory.

12 Claims, 4 Drawing Sheets

OTHER PUBLICATIONS

Figure 1:
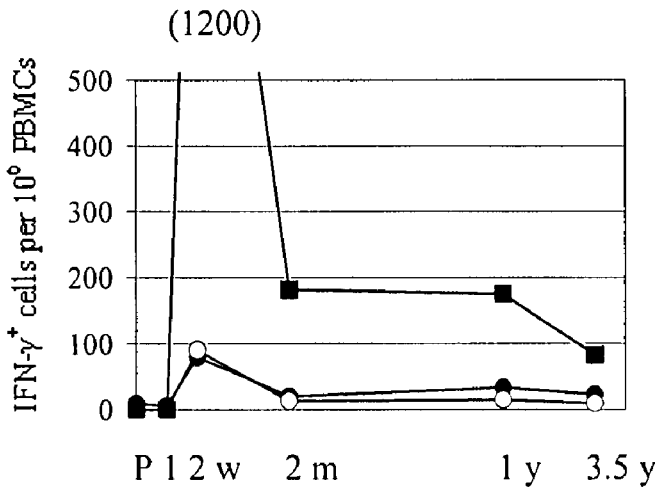
Figure 1:
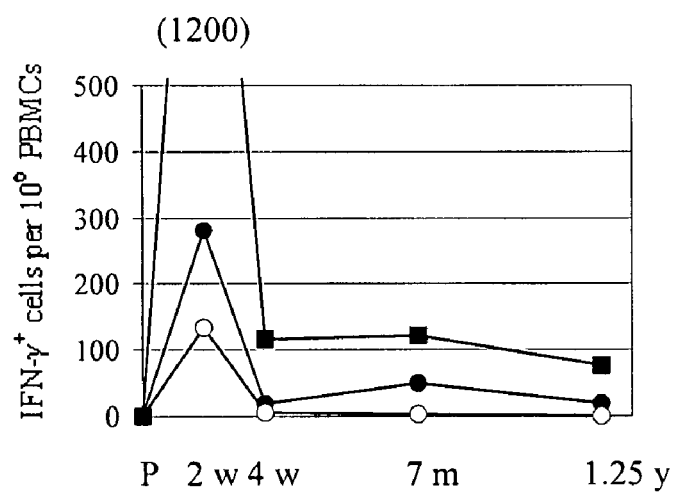
Figure 1:
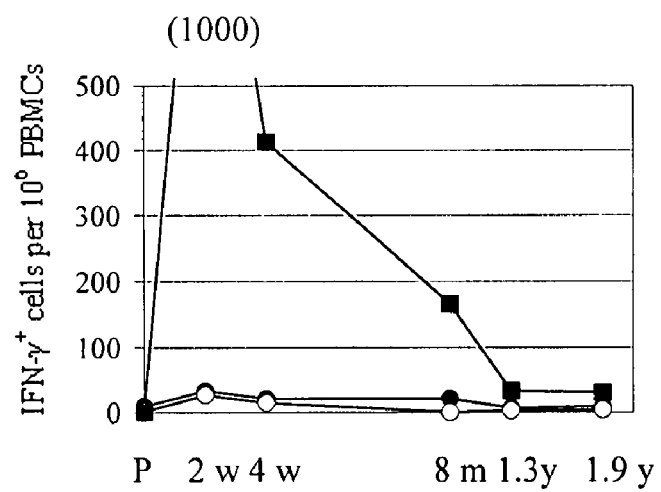

Geysen, H.M., et al., "The Delineation of Peptides Able to Mimic Assembled Epitopes," In *Synthetic Peptides as Antigens—Ciba Foundation Symposium 119* (Porter, R., and Whelan, J., Eds.), pp. 130-149, John Wiley & Sons, Chichester (1986).

Mathew, A., et al., "Identification of Murine Poxvirus-Specific CD8+ CTL Epitopes with Distinct Functional Profiles," *J. Immunol.* 174:2212-2219 (2005).

Tscharke, D.C., et al., "Identification of Poxvirus CD8+ T Cell Determinants to Enable Rational Design and Characterization of Smallpox Vaccines," *J. Exp. Med.* 201(1):95-104 (2005).

Gen Bank Acc. No. Y16780, "Variola Minor Virus Complete Genome," (2005), [online][retrieved on Nov. 14, 2005].

Gen Bank Acc. No. X69198, "Variola Virus DNA Complete Genome," (2005), [online][retrieved on Nov. 14, 2005].

Gen Bank Acc. No. L22579, "Variola Major Virus (Strain Bangladesh—1975) Complete Genome," (1995), [online][retrieved on Nov. 14, 2005].

Gen Bank Acc. No. AF095689, "Vaccinia Virus (Strain Tian Tan) Complete Genome," (2000), [online][retrieved on Nov. 14, 2005].

Gen Bank Acc. No. M35027, "Vaccinia Virus, Complete Genome," (1993), [online][retrieved on Nov. 14, 2005].

Gen Bank Acc. No. U94848, "Vaccinia Virus Strain Ankara, Complete Genomic Sequence," (2003), [online][retrieved on Nov. 14, 2005].

Gen Bank Acc. No. AF482758, "Cowpox Virus Strain Brighton Red, Complete Genome," (2003), [online][retrieved on Nov. 14, 2005].

Gen Bank Acc. No. AF380138, "Monkeypox Virus Strain Zaire-96-I-16, Complete Genome," (2001), [online][retrieved on Nov. 14, 2005].

Bixler, G.S. and Atassi, M.Z., "Molecular Localization of the Full Profile of The Continuous Regions Recognized by Myoglobin Primed T-Cells Using Synthetic Overlapping Peptides Encompassing the Entire Molecule," *Immunological Communications* 12(6):593-603 (1983).

Skelton, N.J., et al., "Proton NMR Assignments and Solution Conformation of RANTES, a Chemokine of the C-C Type," *Biochem.* 34:5329-5342 (1995).

Lazar, E. et al., "Transforming Growth Factor α: Mutation of Aspartic Acid 47 and Leucine 48 Results in Different Biological Activies," *Molecular and Cellular Biology*, 8(3)3:1247-1252 (1988).

Smilek, D.E., et al., "A Single Amino Acid Change in a MYelin Basic Protein Peptide Confers the Capacity to Prevent RAtehr than Induce Experimental Autoimmune Encephalomyelitis," *Proc. Natl. Acad. Sci. USA* 88:9633-9637 (1991).

Ennis, F.A., et al., "Primary Induction of Human CD8+ Cytotoxic T Lymphocytes and Interferon-γ-Producing T Cells After Smallpox Vaccination," *The Journal of Infectious Diseases*, 185:1657-1659 (2002).

Demkowicz, Jr., W.E. and Ennis, F.A., "Vaccinia Virus-Specific CD8+ Cytotoxic T Lymphocytes in Humans," *Journal of Virology*, 67(3):1538-1544 (1993).

Romieu, R., et al., "IFN-γ-secreting $T_h$ Cells Regulate Both the Frequency and Avidity of Epitope-specific CD8+ T Lymphocytes Iduced by Peptide Immunization: an Ex Vivo Analysis," *International Immunology*, 10(9):1273-1279 (1998).

Gen Bank Acc. No. X94355, "Cowpox Virus Strain GRI-90, Complete Genome," (2005), [online][retrieved on Nov. 14, 2005].

Mailing Date Jan. 22, 2009, Non-Final Rejection, U.S. Appl. No. 11/238,122.

Mailing Date Apr. 17, 2009, Response to Non-Final Rejection, U.S. Appl. No. 11/238,122.

Mailing Date Jul. 21, 2009, Examiner Interview Summary Record, U.S. Appl. No. 11/238,122.

Mailing Date Jul. 21, 2009, Restriction Requirement, U.S. Appl. No. 11/238,122.

Mailing Date Aug. 21, 2009, Response to Restriction Requirement, U.S. Appl. No. 11/238,122.

Mailing Date Dec. 29, 2009, Non-Final Rejection, U.S. Appl. No. 11/238,122.

Mailing Date Dec. 29, 2009, Examiner Interview Summary Record, U.S. Appl. No. 11/238,122.

Mailing Date Aug. 11, 2005, Notification Concerning Transmittal of International Preliminary Report on Patentability and International Preliminary Report on Patentability, PCT/US2004/002141.

Mailing Date Nov. 11, 2009, Result of Consultation by telephone with the applicant /representative, EP 04 705 315.2.

Mailing Date Dec. 4, 2009, Letter accompanying subsequently filed items and matter concerning the application, EP 04 705 315.2.

Mailing Date Jan. 19, 2010, Communication pursuant to Article 94(3) EPC, EP 04 705 315.2.

\* cited by examiner

Donor 1

Donor 2

Donor 3

SEQUENCE LISTING

<160> NUMBER OF SEQ ID NOS: 33

<210> SEQ ID NO 1
<211> LENGTH: 9
<212> TYPE: PRT
<213> ORGANISM: Unknown
<220> FEATURE:
<223> OTHER INFORMATION: 74A peptide of MVA

<400> SEQUENCE: 1

Cys Leu Thr Glu Tyr Ile Leu Trp Val
 1               5

<210> SEQ ID NO 2
<211> LENGTH: 9
<212> TYPE: PRT
<213> ORGANISM: Unknown
<220> FEATURE:
<223> OTHER INFORMATION: 165 peptide of MVA

<400> SEQUENCE: 2

Lys Val Asp Asp Thr Phe Tyr Tyr Val
 1               5

<210> SEQ ID NO 3
<211> LENGTH: 9
<212> TYPE: PRT
<213> ORGANISM: Unknown
<220> FEATURE:
<223> OTHER INFORMATION: 165 peptide of Monkeypox (Zaire-96-I-16)

<400> SEQUENCE: 3

Lys Val Asp Tyr Thr Leu Tyr Tyr Val
 1               5

<210> SEQ ID NO 4
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 4

Ile Leu Thr Glu Tyr Ile Leu Trp Val
 1               5

<210> SEQ ID NO 5
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 5

Leu Leu Thr Glu Tyr Ile Leu Trp Val
 1               5

<210> SEQ ID NO 6
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 6

```
Phe Leu Thr Glu Tyr Ile Leu Trp Val
 1               5

<210> SEQ ID NO 7
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 7

Cys Leu Ala Glu Tyr Ile Leu Trp Val
 1               5

<210> SEQ ID NO 8
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 8

Cys Leu Tyr Glu Tyr Ile Leu Trp Val
 1               5

<210> SEQ ID NO 9
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 9

Cys Leu Phe Glu Tyr Ile Leu Trp Val
 1               5

<210> SEQ ID NO 10
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 10

Cys Leu Thr Glu Ile Ile Leu Trp Val
 1               5

<210> SEQ ID NO 11
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 11

Cys Leu Thr Glu Lys Ile Leu Trp Val
 1               5

<210> SEQ ID NO 12
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 12

Cys Leu Thr Glu Asn Ile Leu Trp Val
```

```
                                    1               5

<210> SEQ ID NO 13
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 13

Cys Leu Thr Glu Tyr Ile Ala Trp Val
  1               5

<210> SEQ ID NO 14
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 14

Cys Leu Thr Glu Tyr Ile Tyr Trp Val
  1               5

<210> SEQ ID NO 15
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 15

Cys Leu Thr Glu Tyr Ile His Trp Val
  1               5

<210> SEQ ID NO 16
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 16

Ile Leu Ala Glu Tyr Ile Leu Trp Val
  1               5

<210> SEQ ID NO 17
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 17

Ile Leu Ala Glu Ile Ile Leu Trp Val
  1               5

<210> SEQ ID NO 18
<211> LENGTH: 9
<212> TYPE: PRT
<213> ORGANISM: Unknown
<220> FEATURE:
<223> OTHER INFORMATION: Possible mutant of 74A peptide

<400> SEQUENCE: 18

Ile Leu Ala Glu Ile Ile Ala Trp Val
  1               5
```

```
<210> SEQ ID NO 19
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 19

Ile Val Asp Asp Thr Phe Tyr Tyr Val
 1               5

<210> SEQ ID NO 20
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 20

Leu Val Asp Asp Thr Phe Tyr Tyr Val
 1               5

<210> SEQ ID NO 21
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 21

Phe Val Asp Asp Thr Phe Tyr Tyr Val
 1               5

<210> SEQ ID NO 22
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 22

Lys Val Ala Asp Thr Phe Tyr Tyr Val
 1               5

<210> SEQ ID NO 23
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 23

Lys Val Tyr Asp Thr Phe Tyr Tyr Val
 1               5

<210> SEQ ID NO 24
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 24

Lys Val Phe Asp Thr Phe Tyr Tyr Val
 1               5
```

```
<210> SEQ ID NO 25
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 25

Lys Val Asp Asp Ile Phe Tyr Tyr Val
  1               5

<210> SEQ ID NO 26
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 26

Lys Val Asp Asp Lys Phe Tyr Tyr Val
  1               5

<210> SEQ ID NO 27
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 27

Lys Val Asp Asp Tyr Phe Tyr Tyr Val
  1               5

<210> SEQ ID NO 28
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 28

Lys Val Asp Asp Thr Phe Ala Tyr Val
  1               5

<210> SEQ ID NO 29
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 29

Lys Val Asp Asp Thr Phe His Tyr Val
  1               5

<210> SEQ ID NO 30
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 30

Ile Val Ala Asp Thr Phe Tyr Tyr Val
  1               5
```

-continued

```
<210> SEQ ID NO 31
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 31

Ile Val Ala Asp Ile Phe Tyr Tyr Val
 1               5

<210> SEQ ID NO 32
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 32

Ile Val Ala Asp Ile Phe Ala Tyr Val
 1               5

<210> SEQ ID NO 33
<211> LENGTH: 9
<212> TYPE: PRT
<213> ORGANISM: Unknown
<220> FEATURE:
<223> OTHER INFORMATION: Possible mutant of 165 peptide

<400> SEQUENCE: 33

Leu Val Tyr Asp Lys Phe His Tyr Val
 1               5
```

US 7,803,566 B2

IDENTIFICATION OF GENE SEQUENCES AND PROTEINS INVOLVED IN VACCINIA VIRUS DOMINANT T CELL EPITOPES

RELATED APPLICATION

This application is a continuation of U.S. application Ser. No. 10/764,985, filed Jan. 26, 2004, now U.S. Pat. No. 7,217,526, which claims the benefit of U.S. Provisional Application No. 60/442,846, filed Jan. 24, 2003. The entire teachings of the above applications are incorporated herein by reference.

GOVERNMENT SUPPORT

The invention was supported, in whole or in part, by a grant PO1 AI-49320 and a subcontract, AI-46725 from the National Institutes of Health/National Institute of Allergy and Infectious Diseases. The Government has certain rights in the invention.

BACKGROUND OF THE INVENTION

Immunization with vaccinia virus resulted in long-lasting protection against smallpox and was the successful approach used to eliminate natural smallpox infections worldwide. This accomplishment was achieved without a detailed understanding of human T cell responses to poxviruses. Due to the concern about the potential use of smallpox virus as a bioweapon, smallpox vaccination is currently being reintroduced. However, severe and life threatening complications from vaccination were associated with congenital or acquired T cell deficiencies, but not with congenital agammaglobulinemia. Considering the high incidence of side effects from current smallpox vaccine, the development of a safer, but equally effective vaccine is very important. Thus, it is important to have a detailed understanding of human T cell responses to poxviruses.

Vaccinia-specific CD4+ and CD8+ T cells have been detected in humans and the number of vaccinia virus-specific T cell responses to smallpox vaccine have been measured. Additionally, an intracellular cytokine staining assay was applied to quantitate and characterize vaccinia-specific T cells in mice. However, no T cell epitopes have been identified in humans or mice systems. One major obstacle is the size of the virus. Vaccinia is a large virus with an approximately 200-kbp DNA genome that has approximately 200 open reading frames.

In order to analyze T cell responses to licensed and experimental smallpox vaccines at the single cell level, it is essential to identify CD8+ T cell epitopes. In addition to emphasizing the importance of T cells in the immunity to smallpox, there is a critical need to develop new vaccines safe for use in T cell deficient populations. This information will be useful for the design and analyses of the immunogenicity of experimental vaccinia vaccines, and for basic studies of human T cell memory.

SUMMARY OF THE INVENTION

The present invention relates to the identification of gene sequences and proteins involved in vaccinia virus dominant T cell epitopes. In one embodiment, the invention provides a method for immunizing an individual against infection by vaccinia and/or variola virus, the method comprising inducing an immune response against a polypeptide comprising peptide 74A. In this embodiment, the polypeptide can be selected from the group consisting of MVA189R, Copenhagen B22R, Copenhagen C16L, Bangladesh-1975 D2L, India-1967 D1L, Garcia-1966 B1L, Brighton Red V212 or Zaire-96-I-16 N1R or other homologues of vaccinia and variola virus. In another embodiment, the method can further comprise a second polypeptide comprising peptide 165. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 165. In this embodiment, the polypeptide can be selected from the group consisting of MVA018L, Copenhagen C7L, Tian Tan TC7L, Bangladesh-1975 D11L, India-1967 D8L, Garcia-1966 B14L, Brighton Red V028 or Zaire-96-I-16 D10L or other homologues of vaccinia and variola virus. In a further embodiment, the method can further comprise a second polypeptide comprising peptide 74A. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 74A, immunogenic fragments or mutants thereof. From 1 to about 4 amino acids can be substituted to make up the immunogenic fragments or mutants of peptide 74A, without essentially detracting from the immunological properties of peptide 74A. In this embodiment, the polypeptide can be selected from the group consisting of MVA189R, Copenhagen B22R, Copenhagen C16L, Bangladesh-1975 D2L, India-1967 D1L, Garcia-1966 B1L, Brighton Red V212 or Zaire-96-I-16 N1R or other homologues of vaccinia and variola virus. In another embodiment, the method can further comprise a second polypeptide comprising peptide 165, immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 165, immunogenic fragments or mutants thereof. From 1 to about 4 amino acids can be substituted to make up the immunogenic fragments or mutants of peptide 165, without essentially detracting from the immunological properties of peptide 165. In this embodiment, the polypeptide can be selected from the group consisting of MVA018L, Copenhagen C7L, Tian Tan TC7L, Bangladesh-1975 D11L, India-1967 D8L, Garcia-1966 B14L, Brighton Red V028 or Zaire-96-I-16 D10L or other homologues of vaccinia and variola virus. In another embodiment, the method can further comprise a second polypeptide comprising peptide 74A, immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

The present invention also relates to a method of identifying the presence of vaccinia, variola or other related poxvirus in a sample comprising determining whether T cells present in the sample (e.g., blood, lymph and tissue) become activated in the presence of a polypeptide selected from the group consisting of: peptide 74A (SEQ ID NO: 1), peptide 165 (SEQ ID NO: 2) and a combination thereof, wherein if the T cells become activated, then vaccinia, variola or other related poxvirus is present in the sample. Whether the T cells present in the sample become activated can be determined using, for example, a cytokine assay (e.g., ELISPOT), a flow cytometry assay (e.g., tetramer staining assay) and/or a limiting dilution assay.

T cells can be present in the original sample or can be added to the sample. For example, the sample can be blood which contains T cells. In this embodiment, whether the T cells become activated in the presence of the polypeptide is determined, wherein if the T cells become activated, then vaccinia, variola or other related poxvirus is present in the sample. In another embodiment, the sample does not initially contain T cells. In this embodiment, the sample is contacted with T cells that become activated in the presence of a vaccinia, variola or other related poxvirus. Then whether the T cells become activated in the presence of the polypeptide is determined, wherein if the T cells become activated, then vaccinia, variola and/or other related poxvirus is present in the sample.

The present invention also relates to a method of determining whether an individual has been infected with vaccinia, variola or other related poxvirus comprising determining whether the individual's T cells become activated in the presence of polypeptide selected from the group consisting of: peptide 74A (SEQ ID NO: 1), peptide 165 (SEQ ID NO: 2) and a combination thereof, and wherein if the individual's T cells become activated in the presence of the peptide, then the individual has been infected with vaccinia, variola or other related poxvirus.

A method of monitoring the effectiveness of a vaccinia, variola or other related poxvirus vaccine in an individual who has been administered the vaccinia vaccine is also encompassed by the present invention. The method comprises determining whether the individual's T cells become activated in the presence of a polypeptide selected from the group consisting of: peptide 74A (SEQ ID NO: 1), peptide 165 (SEQ ID NO: 2) and a combination thereof, wherein if the individual's T cells become activated, then the vaccine is effective in the individual. In one embodiment, the vaccine is a vaccinia virus vaccine. In another embodiment, the vaccinia virus vaccine is a cancer vaccine.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIG. 1 is a schematic depicting the kinetics of the frequency of IFN-γ-producing cells specific to these peptides and to whole vaccinia virus quantitated by IFN-γ ELISPOT assay using the peripheral blood mononuclear cells (PBMCs) of the vaccinia-immune donors. Closed circle: peptide 74A-specific cells. Open circle: peptide 165-specific cells. Closed square: vaccinia virus-specific cells. P: pre-immunization.

FIG. 2 depicts FACS staining to confirm specificity of MVA74A and MVA165 tetramers. HLA-A0201-negative donor PBMC was mixed with $CD8^+$ T cell clones specific for either the MVA74A or the MVA165 vaccinia virus epitope at a ratio of 10:1. Four color FACS analysis was done to determine the specificity. Cells are gated on $CD3^+$ $CD4^-$ cells with tetramer on the X-axis and CD8 on the y-axis.

FIG. 3 is a schematic depicting the quantitation of vaccinia virus epitope-specific $CD8^+$ T cells by HLA-A0201/peptide 74A tetramer staining (top) and HLA-A0201/peptide 165 tetramer staining (bottom) of PBMCs of donor 1. Cells were gated on $CD3^+$ and $CD4^-$ cells with tetramer staining on the x-axis and CD8 on the y-axis. The larger squares show $CD8^+$ cells and the smaller squares show $CD8^+$ and $tetramer^+$ cells.

FIG. 4 is a schematic depicting the kinetics of the frequency of $CD8^+$ T cells specific for each epitope quantitated by tetramer staining in PBMCs of three donors after primary immunization. Closed circle: 74A-specific. Open circle: 165-specific. P: pre-immunization. Frequency is calculated per million PBMC for comparison with the data from epitope-specific IFN-γ ELISPOT assays.

DETAILED DESCRIPTION OF THE INVENTION

A description of preferred embodiments of the invention follows.

Successful vaccines deliver to a host one or more antigens derived from a pathogen, thereby stimulating an immune response which protects against subsequent challenge with the pathogen. Such vaccines can take a variety of forms, including attenuated or killed pathogens, for example, viruses or bacteria; one or more proteins or peptides derived from a pathogen or synthetic or recombinant versions of such proteins or peptides; or one or more nucleic acid molecules encoding one or more proteins or peptides from the pathogen, such as a naked DNA vaccine or a nucleic acid molecule administered in a suitable vector, such as a recombinant virus or bacterium or an immunostimulating complex. Vaccines against cell proliferative diseases, such as cancers, typically utilize proteins or fragments thereof, or nucleic acid molecules encoding proteins or fragments thereof, which are unique to diseased cells or generally more abundant in diseased cells compared to healthy cells.

Cell-mediated immunity is dependent upon lymphocytes known as B cells and T cells. B cells produce antibodies targeted against extracellular antigens. T cells recognize antigen fragments (peptides) which are displayed at the surface of a host cell. Such antigen fragments result from uptake of the antigen by a host cell, or synthesis of the antigen within the host cell, followed by cleavage of the antigen within the cell.

Foreign proteins which are synthesized within the host cell or are taken up by the host cell via specific receptors are fragmented within the cytosol of the cell. One or more of the resulting peptides can become associated with class I major histocompatibility molecules (MHC I), and the resulting complexes are then presented at the surface of the cell. These MHC I/peptide complexes are recognized by specific T cell receptors in certain $CD8^+$ T cells, and the peptides so presented are referred to as CD8 epitopes.

A foreign protein can be taken up by a host cell nonspecifically via endocytosis and then fragmented into peptides in a cellular lysosomal or endosomal compartment. One or more of these peptides can then become associated with a class II major histocompatibility molecule (MHC II) to form a complex which is then presented at the surface of the host cell.

These MHC II/peptide complexes are recognized by CD4+ T cells expressing a specific receptor which recognizes the MHC II/peptide complex. These peptides are referred to as CD4 epitopes.

Peripheral T cells in the blood and organs of the immune system (e.g. spleen and lymph nodes) exist in a quiescent or resting state. Upon interaction of T cells with an MHC/epitope complex, the T cells proliferate and differentiate into activated cells having a variety of functions. CD8+ T cells typically become cytotoxic upon activation and destroy antigen-presenting cells via direct contact. Activated CD4+ T cells provide a helper function to B cells, enabling B cells to differentiate into antibody-producing cells. Activated CD8+ T cells and CD4+ T cells release a variety of cytokines (lymphokines or interleukins), which can, for example, control differentiation of many classes of lympholytic precursor cells.

The present invention relates to vaccinia virus-specific CD8+ cytotoxic T lymphocyte (CTL) lines that were established by limiting dilution cloning from the peripheral blood mononuclear cells (PBMCS) of HLA-A0201-positive donors who received primary immunization with the licensed smallpox vaccine, Dryvax®. Among the highly polymorphic human MHC class I genes, HLA-A0201 was chosen to identify CD8+ T cell epitopes because of the commonality of this allele among most ethnic groups. HLA-A0201 peptide binding motif searches was performed on all of the protein sequences of the modified vaccinia virus Ankara (MVA) strain (GenBank accession number U94848), which is being proposed for use as an attenuated smallpox vaccine and as a vector for vaccination against other infectious agents. The computer algorithm "HLA Peptide Binding Predictions" (on the World Wide Web at: bimas.dcrt.nih.gov/molbio/hla_bind/ visited on Aug. 20, 2001 and Aug. 21, 2001) was used to calculate the binding affinity (score) of 9mer peptides to the HLA-A0201 molecule. It was hypothesized that early gene products may be more likely to have CD8+ T cell epitopes, since in both humans and mice all of the known CD8+ T cell epitopes to cytomegalovirus are encoded by immediate-early phase proteins. The early, early and late, and late genes in vaccinia were categorized by nucleotide sequence motifs, such as a late promoter or an early termination motif. For initial screening all peptides with; (1) a binding score of more than a 1000 (70 peptides); or (2) a binding score of 100 to 999 and encoded by a gene expressed early or both early and late (125 peptides) were synthesized. A total of 195 peptides were screened using fifteen vaccinia virus-specific CTL lines. Two T cell epitopes were restricted by HLA-A0201 and cross-reactive to MVA.

One CTL line, VA55 3.13, recognized peptide 74A, CLTEYILWV (SEQ ID NO: 1), in a 21.7K protein encoded by a putative early and late gene, "189R", of the MVA strain with a calculated binding score of 3607. Another CTL line, VA49 3.12, recognized peptide 165, KVDDTFYYV (SEQ ID NO: 2), which is in a host range protein encoded by a putative early and late gene, "018L", with a calculated binding score of 365. FIG. 1 demonstrates the high level of specific recognition by these CTL lines of their respective epitope peptides (i.e., peptide 74A or peptide 165) in a dose response CTL experiment. These epitope sequences are highly-conserved in vaccinia and variola viruses (Table 1).

TABLE 1

Conservation of epitopes among poxviruses causing infection in human Only

| | GenBank accession # | Gene name | 74A peptide | Gene name | 165 peptide |
|---|---|---|---|---|---|
| Vaccinia | | | | | |
| MVA | U94848 | 189R | CLTEYILWV (SEQ ID NO: 1) | 018L | KVDDTFYYV (SEQ ID NO: 2) |
| Copenhagen Tian Tan[a] | M35027 AF095689 | B22R & | ********* | C7L TC7L | ********* ********* |
| Variola | | | | | |
| Bangladesh-India-1967 | L22579 X69198 | D2L D1L | ********* ********* | D11L D8L | ********* ********* |
| Variola | | | | | |
| Garcia-1966 | Y16780 | B1L | ********* | B14L | ********* |
| Cowpox | | | | | |
| Brighton Red | AF482758 | V212 | ********* | V028 | ********* |
| Monkeypox | | | | | |
| Zaire-96-I-16 | AF380138 | N1R | ********* | D10L | ***Y*L*** (SEQ ID NO: 3) |

Only strains of which complete genome has been sequenced are listed.
\* indicate identical amino acid.
[a]Tian Tan strain does not have 189R orthologue according to the nucleotide sequence.
[b]Both genes are located within the inverted terminal repeats and the gene sequences are identical.

Epitope-specific T cell clones can be generated using methods which are generally known in the art (see, for example, Fathman, et al., in Paul, ed., *Fundamental Immunology*, second edition, Raven Press (1989), Chapter 30, the contents of which are hereby incorporated by reference in their entirety). The isolation of epitope-specific T cell clones is based on T cell biology. Generally, an animal, such as a mouse, is immunized with a preparation of antigens (a bacterial lysate, or a purified protein) or is infected with a virus, such as a wild type virus or a recombinant virus containing heterologous genes encoding one or more proteins from a pathogenic microorganism, such as a virus. The animal is then sacrificed and the peripheral blood mononuclear cells (PBMC: includes T cells, B cells, monocytes), spleen and lymph nodes are isolated. The isolated cells are then cultured in media containing a defined component of the original antigenic preparation, often a recombinant or purified protein, and the essential T cell growth factor interleukin-2 (IL-2). The only T cells which will proliferate are those which recognize MHC/epitope complex in which the epitope is derived from the antigenic preparation. These cells become activated and proliferate while the unactivated cells begin to die. The cultures are maintained for several weeks, with the media containing antigen and IL-2 being periodically replaced. Eventually, clusters of living and dividing cells (a T cell line) can be observed in some of the cultures.

The proliferating cells are generally not clonal at this point and are of limited use for assaying epitope specific T cell responses. The T cell line is, preferably, cloned through a process referred to as limiting dilution. In this method, PBMC are isolated from, for example, the same strain as the original used to isolate the T cell line. These cells, called antigen presenting cells, will serve as a source of MHC proteins and will present the MHC:peptide complex to the T cell line. The T cell line is diluted to a concentration of about 1 to 5 T cells/mL in a suspension of APCs that contains the antigen of interest and IL-2. This suspension is then transferred into, for example, round or "v"-bottom 96 well microtitre plates, so that each well contains, on average, no more than 1 T cell. The cultures are maintained for several weeks and a clone can grow out of one or more cultures. The cells isolated by limiting dilution are the progeny of a single cell that expresses only one T cell receptor, and the clone is thus epitope-specific.

Figure 2:
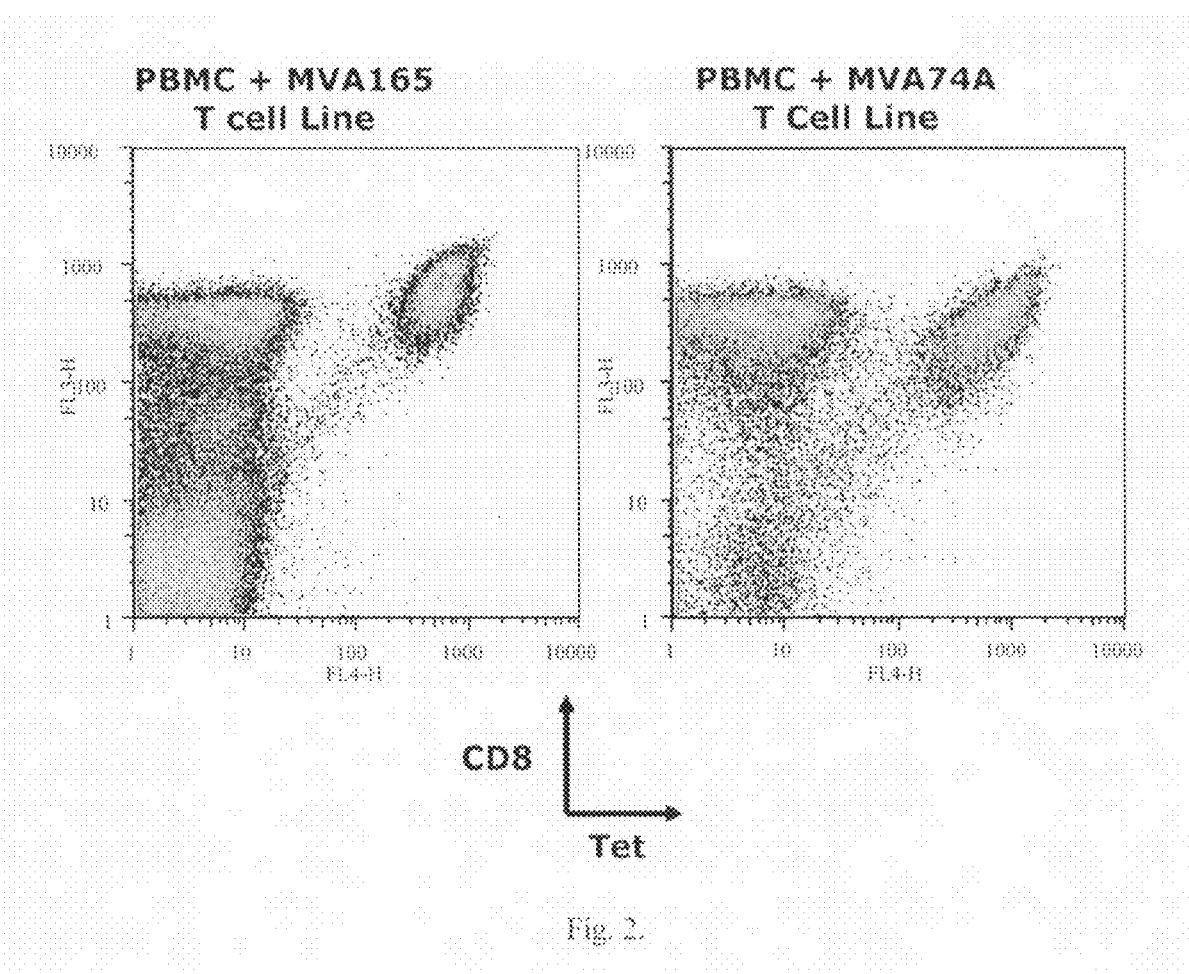
Figure 3:
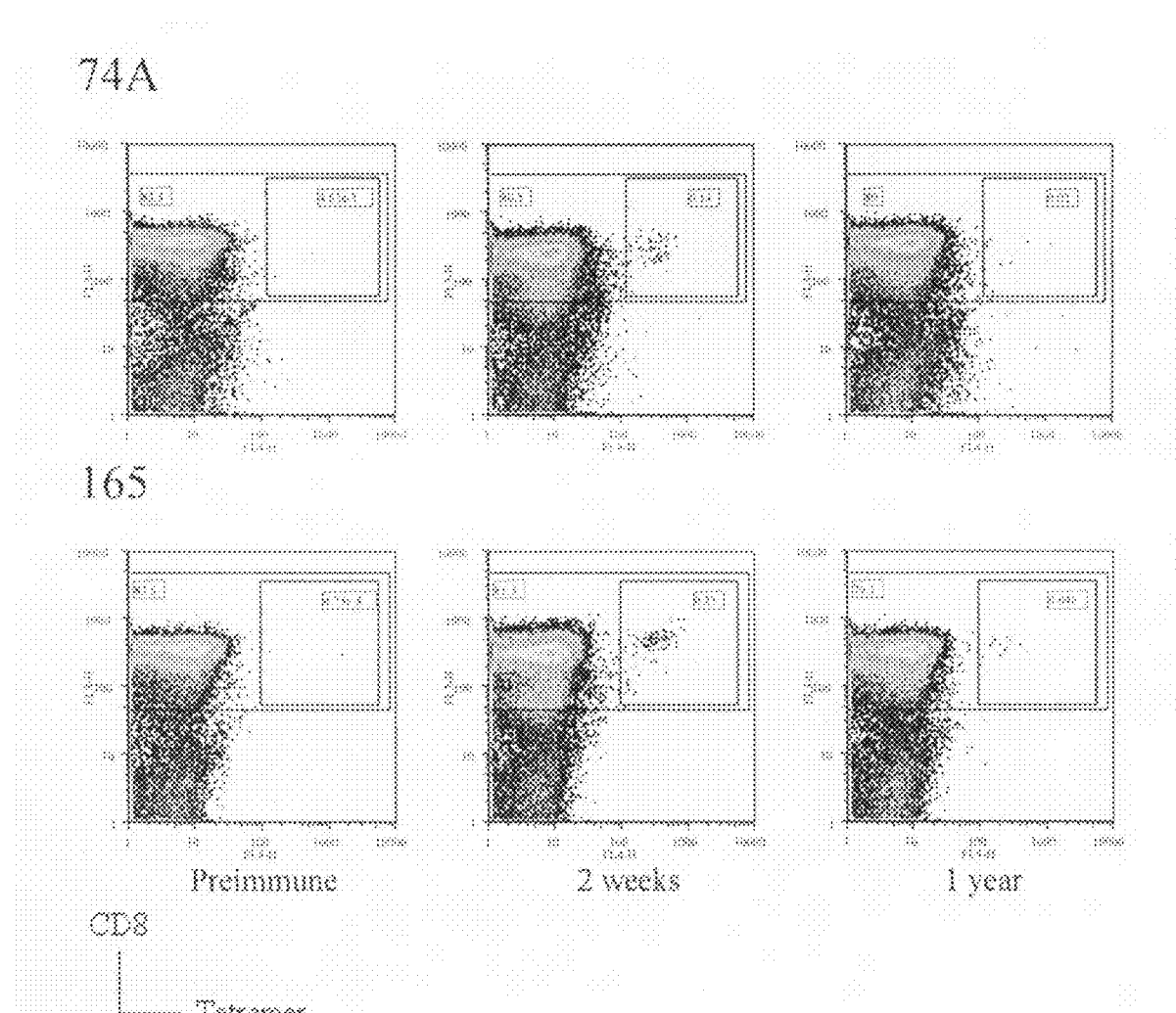
Figure 4:
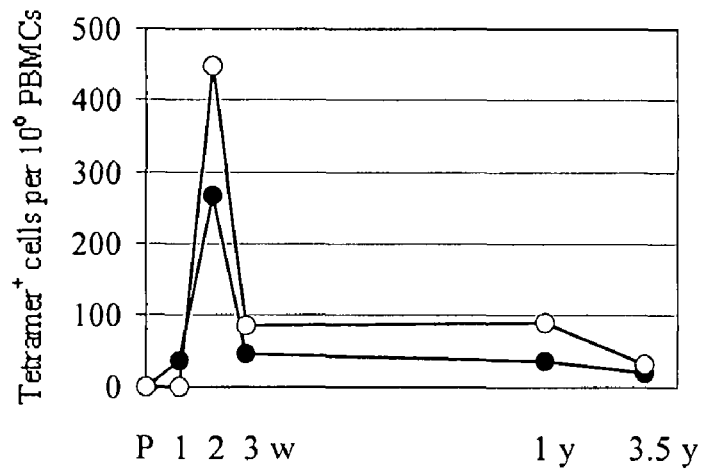
Figure 4:
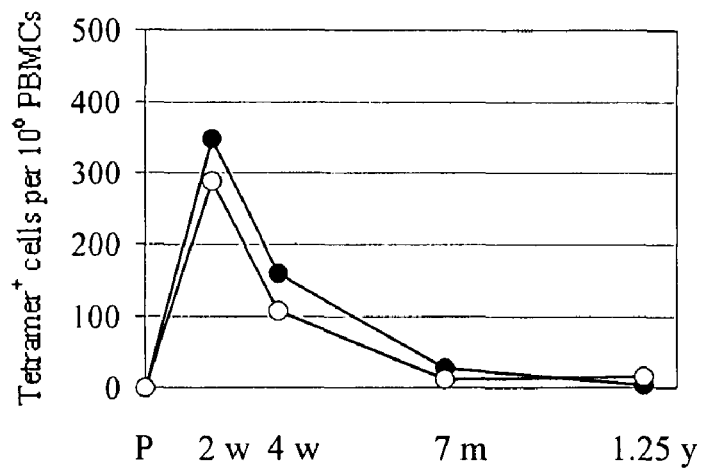
Figure 4:
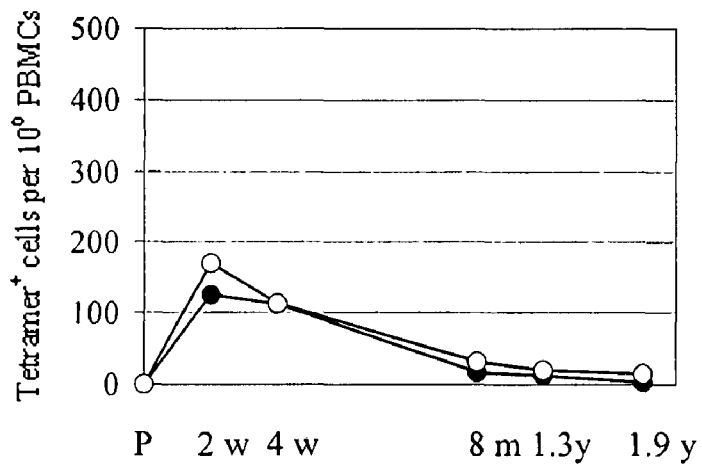

CD8$^+$ T cells specific to these epitopes were measured at several time points following primary immunization by peptide/HLA-A0201 tetramer staining using the PBMCs of three HLA-A0201-positive donors. FIG. 2 shows representative FACS plots of donor 1 PBMC. In FIGS. 3 and 4, "preimmune" means prior to primary first immunization, and "two weeks" means two weeks after the second immunization for donor 3 who failed to "take" after primary immunization, and twenty days after primary immunization was immunized for the second time. In all three donors the frequency of vaccinia-specific CD8$^+$ T cells peaked two weeks after primary immunization and then declined, but were still detectable one to three years following primary immunization (FIG. 3). Two weeks after vaccination the IFN-γ-producing cells specific to these two epitopes were 14% of total vaccinia virus-specific IFN-γ-producing cells in donor 1, 35% in donor 2, and 6% in donor 3 (FIG. 4).

Thus, two CD8$^+$ T cell epitopes restricted by HLA-A0201, the most common MHC class I allele in humans have been identified. These are the first T cell epitopes that have been reported for vaccinia virus. IFN-γ-producing cells specific to these two epitopes represented 6 to 35% of total number of IFN-γ-producing cells specific to vaccinia virus. The frequency of epitope-specific T cells was always higher by peptide/HLA tetramer staining than by IFN-γ-ELISPOT assay, although post-vaccination kinetics for each epitope-specific T cell was similar using both methods.

As for epitope selection, peptide 74A was the 15$^{th}$ highest binding peptide to HLA-A0201 of the 195 peptides selected for screening and peptide 165 was the 95$^{th}$ highest binder. One common characteristic of these two peptides is that they are both encoded by genes with a late promoter and an early termination motif, which means they may be expressed at both early and late phases of infection. The 189R gene of MVA strain encoding peptide 74A is a nonessential gene with unknown function. The 018L gene of MVA encoding peptide 165 is an orthologue of the host range protein, C7L, of the Copenhagen strain. Although selection of peptides was biased toward genes expressed in the early phase of infection, viral proteins produced in the early phase of infection may be processed and presented more efficiently by infected cells than those produced only in late phase, as a result of vaccinia virus down regulating host protein synthesis. These two epitopes are highly-conserved among variola viruses, suggesting the CTLs recognizing these epitopes will recognize variola virus-infected cells.

In one embodiment, the invention provides a method for immunizing an individual against infection by vaccinia and/or variola virus, the method comprising inducing an immune response against a polypeptide comprising peptide 74A. In this embodiment, the polypeptide can be selected from the group consisting of MVA189R, Copenhagen B22R, Copenhagen C16L, Bangladesh-1975 D2L, India-1967 D1L, Garcia-1966 B1L, Brighton Red V212 or Zaire-96-I-16 N1R or other homologues of vaccinia and variola virus. In another embodiment, the method can further comprise a second polypeptide comprising peptide 165. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 165. In this embodiment, the polypeptide can be selected from the group consisting of MVA018L, Copenhagen C7L, Tian Tan TC7L, Bangladesh-1975 D11L, India-1967 D8L, Garcia-1966 B14L, Brighton Red V028 or Zaire-96-I-16 D1L or other homologues of vaccinia and variola virus. In a further embodiment, the method can further comprise a second polypeptide comprising peptide 74A. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 74A, immunogenic fragments or mutants thereof. From 1 to about 4 amino acids can be substituted to make up the immunogenic fragments or mutants of peptide 74A, without essentially detracting from the immunological properties of peptide 74A. In this embodiment, the polypeptide can be selected from the group consisting of MVA189R, Copenhagen B22R, Copenhagen C16L, Bangladesh-1975 D2L, India-1967 D1L, Garcia-1966 B1L, Brighton Red V212 or Zaire-96-I-16 N1R or other homologues of vaccinia and variola virus. In another embodiment, the method can further comprise a second polypeptide comprising peptide 165, immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

In another embodiment, the present invention relates to a method for immunizing an individual against infection by vaccinia and/or variola virus, the method comprising inducing an immune response against a polypeptide comprising peptide 165, immunogenic fragments or mutants thereof. From 1 to about 4 amino acids can be substituted to make up the immunogenic fragments or mutants of peptide 165, without essentially detracting from the immunological properties of peptide 165. In this embodiment, the polypeptide can be selected from the group consisting of MVA018L, Copenhagen C7L, Tian Tan TC7L, Bangladesh-1975 D11L, India-1967 D8L, Garcia-1966 B14L, Brighton Red V028 or Zaire-96-I-16 D10L or other homologues of vaccinia and variola virus. In another embodiment, the method can further comprise a second polypeptide comprising peptide 74A, immunogenic fragments or mutants thereof. In a further embodiment, the immune response is induced by administering a product selected from the group consisting of a polypeptide, a naked nucleic acid molecule encoding the peptide or a nucleic acid molecule, encoding the peptide, in a suitable vector.

Several methods are described in the literature which are useful for the identification of T cell epitopes. For example, DeLisi et al. have suggested that potential epitopic sites may be located by identification of potential amphipathic alpha helical regions in the molecule. DeLisi et al., *Proc. Natl. Acad. Sci. USA* 82:7048 (1987). Bixler et al. describe a strategy of synthesizing overlapping synthetic peptides encompassing an entire protein molecule for delineation of T cell epitopes. Bixler et al., *Immunol. Com.* 12:593 (1983); Bixler et al. *J. Immunogenet.* 11:339 (1994). A synthetic method described by Gysen (*Ciba Foundation Symposium* 119:130 (1986)) permits synthesis of a large variety of peptides thereby mimicking of a variety of potential binding sites, in turn allowing rapid scanning of a molecule.

More traditional methods, such as enzymatic or chemical digestion of proteins provide peptide fragments which may be tested for T cell activity. For example, enzymes such as chymotrypsin, elastase, ficin, papain, pepsin, or trypsin provide limited and predictable fragments by cleavage of specified amino acid linkages; similarly chemical compounds such as N-chloro-succinimide BPNS-skatole, cyanogen bromide, formic acid, or hydroxylamine, also produce definable fragments by their action on proteins. The presence of the desired T cell stimulating activity in any given fragment can be determined by subjecting purified fragments to a standard T cell proliferation assay, or by analyzing unpurified fragments with a T cell Western Assay. Young et al., *Immunol.* 59:167 (1986).

Peptide 74A and peptide 165 of the invention are CD8 epitopes and the T cells specific for these peptides are CD8+ T cells. The effector functions of CD8+ T cells include lysis of antigen presenting cells and release of cytokines. Therefore, the extent of CD8+ T cell response to the antigen presenting cells can be determined using an assay for cell lysis or by measuring the production of one or more cytokines. The CD8+ T cell response can also be measured by measuring the extent of release of one or more cytokines. In general, greater cell lysis activity or cytokine release will correlate with greater immunogenicity.

In one embodiment, the present invention relates to methods for immunizing an individual, particularly a human, against infection by vaccinia and/or variola virus by inducing an immune response against a polypeptide comprising peptide 74A and/or peptide 165. In a further embodiment, the immune response can be induced against a polypeptide comprising an immunogenic fragment or mutant of peptide 74A and/or peptide 165. Although the methods described herein are particularly useful for human immunization, the methods are equally applicable to other mammals. In particular embodiments, the individual is positive for the HLA-A0201 gene.

As used herein the terms "immunogenic fragment" and "mutant" of peptide 74A and/or peptide 165 refer to polypeptides in which 1 to about 4 amino acids have been substituted without essentially detracting from the immunological properties thereof can be generated in a variety of ways. For example, in vitro mutagenic techniques can be used to modify the cloned gene encoding peptide 74A and/or peptide 165. Such methods, which are well known to one skilled in the art, can be used to delete, insert or substitute nucleotides in the gene resulting in the deletion, insertion or substitution of amino acids in the encoded product. Examples of immunogenic fragments or mutants of peptide 74A and peptide 165 include, but are not limited to, those shown in Table 2. The immunological properties of the mutagenized encoded product can be assayed using methods such as those which are well known to one skilled in the art.

TABLE 2

Examples of immunogenic fragments and mutants of peptide 74A and peptide 165.

| Possible Immunogenic fragments or mutants | 74A peptide | 165 peptide |
|---|---|---|
| 1 | ILTEYILWV (SEQ ID NO: 4) | IVDDTFYYV (SEQ ID NO: 19) |
| 2 | LLTEYILWV (SEQ ID NO: 5) | LVDDTFYYV (SEQ ID NO: 20) |
| 3 | FLTEYILWV (SEQ ID NO: 6) | FVDDTFYYV (SEQ ID NO: 21) |
| 4 | CLAEYILWV (SEQ ID NO: 7) | KVADTFYYV (SEQ ID NO: 22) |
| 5 | CLYEYILWV (SEQ ID NO: 8) | KVYDTFYYV (SEQ ID NO: 23) |
| 6 | CLFEYILWV (SEQ ID NO: 9) | KVFDTFYYV (SEQ ID NO: 24) |
| 7 | CLTEIILWV (SEQ ID NO: 10) | KVDDIFYYV (SEQ ID NO: 25) |
| 8 | CLTEKILWV (SEQ ID NO: 11) | KVDDKFYYV (SEQ ID NO: 26) |
| 9 | CLTENILWV (SEQ ID NO: 12) | KVDDYFYYV (SEQ ID NO: 27) |
| 10 | CLTEYIAWV (SEQ ID NO: 13) | KVDDTFAYV (SEQ ID NO: 28) |
| 11 | CLTEYIYWV (SEQ ID NO: 14) | KVDDTFHYV (SEQ ID NO: 29) |
| 12 | CLTEYIHWV (SEQ ID NO: 15) | IVADTFYYV (SEQ ID NO: 30) |
| 13 | ILAEYILWV (SEQ ID NO: 16) | IVADIFYYV (SEQ ID NO: 31) |
| 14 | ILAEIILWV (SEQ ID NO: 17) | IVADIFAYV (SEQ ID NO: 32) |
| 15 | ILAEIIAWV (SEQ ID NO: 18) | LVYDKFHYV (SEQ ID NO: 33) |

Effective dosages for inducing an immune response (also referred to as a virus protective response) against vaccinia and/or variola can be determined empirically with initial dosage ranges based upon historical data for peptide/protein vaccine compositions. As used herein, the terms "induced immune response" or "virus protective response" refers to an immunological response in the individual resulting in the successful control or limitation of infection by vaccinia and/or variola virus which is clinically observed.

For example, individuals can be administered dosages of peptide 74A and/or peptide 165 ranging from 0.5-500 micrograms. Whether a particular dosage is effective can be determined using well known T cell proliferation and cytotoxicity assays. For example, following administration of the protein to an individual blood is drawn. Cytotoxic T cells are identifiable by $^{51}$Cr release assay (see e.g., Kuwano et al., *J. Virol.* 140:1264-1268 (1988)). Helper T cells are identifiable by a standard T cell proliferation assay (see e.g., Kurane et al., *J. Clin. Invest.* 83:506-513 (1989)). The results from these studies are compared with results from the same experiments conducted with T cells from the same individual prior to administration of the antigen. By comparing this data, effective dosage ranges can be determined.

A wide variety of pharmaceutically acceptable carriers are useful. Pharmaceutically acceptable carriers include, for example, water, physiological saline, ethanol polyols (e.g., glycerol or administration is typically parenteral (i.e., intravenous, intramuscular, intraperitoneal or subcutaneous). An adjuvant (e.g., alum) can also be included in the vaccine mixture.

The invention also pertains to a method for immunizing an individual against infection by vaccinia and/or variola virus by administering a vaccine composition comprising at least one essentially pure T cell epitope (i.e., peptide 74A or peptide 165) in combination with a pharmaceutically acceptable carrier. Due to genetic variability between individuals, a single T cell epitope may not stimulate a virus protective response in all individuals to whom it is administered. Therefore, by combining two or more distinct T cell epitopes (i.e., both peptide 74A and peptide 165), the vaccine is more broadly effective. As indicated above, helper T cell epitopes and cytotoxic T cell epitopes are thought to comprise distinct (albeit possibly overlapping) regions of proteins. Cytotoxic T cell epitopes can be distinguished from helper T cells epitopes experimentally using the cytoxicity and proliferation assays described above (helper T cells stimulate proliferation but do not posses cytotoxic activity).

Peptide 74A and/or peptide 165 can be administered as an polypeptide. Such polypeptides can be synthesized chemically. Alternatively, a truncated portion of a gene encoding peptide 74A and/or peptide 165 can be expressed in a cell, and the encoded product can be isolated using know methods (e.g., column chromatography, gel electrophoresis, etc.).

As used herein, the term polypeptide means any amino acid sequence which is identical or substantially homologous to peptide 74A and/or peptide 165. The expression substantially homologous refers to polypeptides having an amino acid sequence of peptide 74A or peptide 165 in which amino acids have been substituted without essentially detracting from the immunological properties thereof. This definition includes amino acid sequences of sufficient length to be classified as oligopeptides (these terms are not used consistently or with great precision in the literature).

In one embodiment, both a helper T cell epitope and a cytotoxic T cell epitope can be administered to the individual. The stimulation of cytotoxic T cells is desirable in that these cells will kill cells infected by vaccinia and/or variola virus. The stimulation of helper T cells is beneficial in that they secrete soluble factors which have a stimulatory effect on other T cells, as well as B cells.

In another embodiment, a gene encoding a protein listed in Table 1, or a portion thereof which contains peptide 74A or peptide 165, can be cloned into a recombinant virus which expresses peptide 74A or peptide 165, or immunogenic fragment or mutant thereof, in the individual to be immunized. An example of such a recombinant virus system is the vaccinia system described by Paoletti et al. (U.S. Pat. No. 4,603,112), the disclosure of which is incorporated herein by reference. Other viruses have been described in the literature which have a genome which can accommodate the insertion of a foreign DNA such that a protein encoded by the DNA is expressed in vivo. Any such recombinant virus is useful for the practice of this invention.

Identification of these epitopes will enable the analysis and quantitation of vaccinia virus-specific CD8$^+$ T cells in the acute and memory phases and to compare CD8$^+$ T cell responses specific to different epitopes. Additionally, expansion and subsequent shrinkage of epitope-specific CD8$^+$ T cells at the T cell receptor level can be monitored. Definition of T cell epitopes will help us to better understand human T cell responses to vaccinia virus as a model of human infection. In addition, it will provide a quantitative measure of poxvirus T cell immunity when these viruses are used as viral vectors.

The present invention also relates to a method of identifying the presence of vaccinia, variola virus and/or other related poxvirus in a sample comprising determining whether T cells present in the sample become activated in the presence of a polypeptide selected from the group consisting of: peptide 74A (SEQ ID NO: 1), peptide 165 (SEQ ID NO: 2), an immunogenic mutant and fragment thereof and a combination thereof, wherein if the T cells become activated, then vaccinia, variola and/or other related poxvirus is present in the sample. In a particular embodiment, the T cells are CD8$^+$ T cells.

As used herein a "sample" for use in the methods of the present invention can be any type of sample that can be analyzed in the method and can be obtained from a variety of sources. T cells can be present in the original sample or can be added to the sample. The sample can be one which is found in any environment, such as an unknown powder or liquid. In addition, the sample can be obtained from a host, such as a mammalian host or individual (e.g., human, canine, feline, bovine, murine). Samples from a host include blood (e.g., whole blood, PMBCs), lymph (e.g., lymph fluid) and tissue (e.g., lymph nodes, spleen). In a particular embodiment, the sample is from an individual that is positive for the HLA-A0201 gene.

For example, the sample can be a sample which does not initially contain T cells. In this embodiment, the sample is contacted with T cells that become activated in the presence of a vaccinia, variola and/or other related poxvirus. Then whether the T cells become activated in the presence of the polypeptide is determined, wherein if the T cells become activated, then vaccinia, variola and/or other related poxvirus is present in the sample. In another embodiment, the sample can be blood which contains T cells. In this embodiment, whether the T cells become activated in the presence of the polypeptide is determined, wherein if the T cells become activated, then vaccinia, variola and/or other related poxvirus is present in the sample.

Thus, the present invention also relates to a method of determining whether an individual has been infected with vaccinia, variola virus and/or other related pox virus comprising determining whether the individual's T cells become activated in the presence of polypeptide selected from the group consisting of: peptide 74A (SEQ ID NO: 1), peptide 165 (SEQ ID NO: 2), an immunogenic mutant or fragment thereof and a combination thereof, and wherein if the individual's T cells become activated in the presence of the peptide, then the individual has been infected with vaccinia, variola and/or other related poxvirus.

As described herein, peripheral T cells in the blood and organs of the immune system (e.g. spleen and lymph nodes) exist in a quiescent or resting state. Upon interaction of T cells with an MHC/epitope complex, the T cells proliferate and differentiate into activated cells having a variety of functions. CD8$^+$ T cells typically become cytotoxic upon activation and destroy antigen-presenting cells via direct contact. Activated CD4$^+$ T cells provide a helper function to B cells, enabling B cells to differentiate into antibody-producing cells. Activated CD8$^+$ T cells and CD4$^+$ T cells release a variety of cytokines (lymphokines or interleukins), which can, for example, control differentiation of many classes of lympholytic precursor cells.

Whether the T cells present in the sample become activated can be determined using a variety of assays known to those of skill in the art. For example, a cytokine assay (e.g., ELISPOT), a flow cytometry assay (e.g., tetramer staining assay), intracellular cytokine staining assay (ICS) and/or a limiting dilution assay (LDA) can be used in the methods of the present invention.

Poxviruses such as vaccinia virus allow for simplified integration of multiple foreign genes with high levels of expression, and thus, are widely used for the cytoplasmic expression of recombinant genes in mammalian cells. Vaccinia virus mutants and other poxviruses are receiving special attention because of their diminished cytopathic effects and increased safety. For example, replicating and non-replicating vectors encoding the bacteriophage T7 RNA polymerase for transcription of recombinant genes and numerous cancer antigens have been engineered (Carroll, M. W. and Moss B., *Curr. Opin. Biotechnol.*, 8(5):573-577 (1997); Carroll, M. W., et al., *Vaccine*, 15(4):387-394 (1997).

The invention also relates to a method of monitoring the effectiveness of a vaccinia, variola and/or other related pox virus vaccine in an individual who has been administered the vaccinia vaccine. The method comprises determining whether the individual's T cells become activated in the presence of a polypeptide selected from the group consisting of: peptide 74A (SEQ ID NO: 1), peptide 165 (SEQ ID NO: 2), an immunogenic mutant or fragment thereof and a combination thereof, wherein if the individual's T cells become activated, then the virus is effective in the individual. In one embodiment, the vaccine is a vaccinia vaccine. In another embodiment, the vaccine is vaccinia virus that is a cancer vaccine.

EXEMPLIFICATION

Donors

Donors in this study were three HLA-A0201-positive laboratory workers received primary immunization by scarification with the licensed smallpox vaccine, Dryvax®, as recommended by the Centers for Disease Control and Prevention for laboratory personnel working with vaccinia viruses. The HLA-A and B alleles of donor 1 were A2 (A0201), B15, B18; those of donor 2 were A2 (A0201), B15, B44; and those of donor 3 were A2 (A0201), A31, B40, B51.

Viruses

Vaccinia virus New York City Board of Health (NYCBH), the same strain used to produce Dryvaxâ, was provided by Gail Mazzara and Dennis Panicali of Applied Biotechnology, Inc, and propagated and titrated in CV-1 cells (ATCC # CCL-70) as previously described (Littuau, R. A., et al., *J. Virol.*, 66:2274-2280 (1992); Terajima, M. et al., *Virus Res.* 84:67-77 (2002)). Modified vaccinia virus Ankara strain (MVA) was kindly supplied by Bernard Moss of National Institute of Allergy and Infectious Diseases/National Institute of Health, and was propagated and titrated in BHK-21 cells (ATCC # CCL-10) following published methods (Carroll, M. W., et al., *Virology* 238:198-211 (1997)).

CTL Lines

Vaccinia virus-specific CTL lines were isolated from peripheral blood mononuclear cells (PBMCs) of immunized donors by limiting dilution cloning (Demkowicz, W. E., et al., *J. Virol.* 67:1538-1544 (1993)). Vaccinia virus NYCBH strain was used to stimulate PBMCs for cloning and to infect target cells for cytotoxicity assays. Cytotoxicity assays were performed as previously described (Frey, S. E., et al., *J. Med.* 346:1275-1280 (2002)). Hmy C1R A2.1 cells (gift from William E. Biddison of NIH/NINDS), which express only HLA-A0201 at normal levels, were used as targets in cytotoxicity assay to confirm the HLA-A0201 restriction. Surface expression of CD4 and CD8 was determined by flow cytometry using FITC-conjugated antibodies (Becton Dickinson). Cross-reactivity of CTL lines was determined using autologous B-LCLs (B-lymphoblastoid cell lines), that were infected with MVA as target cells in cytotoxicity assays.

Screening Peptides in Cytotoxicity Assay

Peptides were synthesized with a Symphony automated peptide synthesizer at the Protein Core Facility in the University of Massachusetts Medical School or purchased from Mimotopes Pty. Ltd. When predicted epitopes overlapped, we made them as a longer peptide fragment. For technical reasons some of these screening peptides were made as a 13mer instead of a 9mer. In screening cytotoxicity assays, mixtures of five peptides were used and the concentration of each peptide was 5 mg/ml. When the peptide recognized was longer than 9 amino acids, truncated 9mer peptide epitopes were constructed and analyzed in cytotoxicity assays. All peptides recognized were tested in dose-response experiments (FIG. 1).

Tetramer Staining

Peptide/HLA-A0201 tetramers were made in the Tetramer Core Facility in the University of Massachusetts Medical School following the protocol published previously (Catalina, M. D., et al., *J. Immunol.*, 167:4450-4457 (2001)). Each lot of tetramer was titrated using CTL lines specific to the peptide mixed with autologous PBMCs at a 1 to 10 (or 20) ratio to determine the optimal concentration for staining.

Interferon (IFN)-g ELISPOT Assay

IFN-g ELISPOT assays were performed as previously described (Ennis, F., et al., *J. Infect. Dis.* 185:1657-1659 (2002)). For stimulation, PBMCs were incubated with vaccinia virus NYCBH strain at an MOI of 1 or with peptide at a final concentration of 10 mg/ml for 16 hours.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method of identifying T cells in a sample that become activated in the presence of a vaccinia or variola virus that comprises a polypeptide having an amino acid sequence that is identical or substantially homologous to peptide 74A (SEQ ID NO: 1) or peptide 165 (SEQ ID NO: 2), comprising contacting the T cells with a peptide selected from the group consisting of peptide 74A (SEQ ID NO: 1); peptide 165 (SEQ ID NO: 2); an immunogenic fragment of peptide 74A or peptide 165, wherein the immunogenic fragment maintains the function of peptide 74A or peptide 165 as a CD8 T cell epitope of the vaccinia or variola virus; an immunogenic mutant of peptide 74A or peptide 165, wherein the immunogenic mutant maintains the function of peptide 74A or peptide 165 as a CD8 T cell epitope of the vaccinia or variola virus, is the same length as peptide 74A or peptide 165, and 1 to 4 amino acids of peptide 74A or peptide 165 are substituted in the immunogenic mutant; and a combination thereof; wherein activation of the T cells by the peptide indicates that the T cells become activated in the presence of the vaccinia or variola virus.

2. The method of claim 1 wherein whether the T cells present in the sample become activated is determined using an assay selected from the group consisting of a cytokine assay, a flow cytometry assay and a limiting dilution assay.

3. The method of claim 2 wherein the cytokine assay is an ELISPOT assay and the flow cytometry assay is a tetramer staining assay.

4. The method of claim 1 wherein the sample is selected from the group consisting of blood, lymph and tissue.

5. The method of claim 4 wherein the sample is a peripheral blood mononuclear cell sample.

6. A method of determining whether an individual has been infected with a vaccinia or variola virus that comprises a polypeptide having an amino acid sequence that is identical or substantially homologous to peptide 74A (SEQ ID NO: 1) or peptide 165 (SEQ ID NO: 2), comprising determining whether the T cells in a sample from the individual become activated in the presence of a peptide selected from the group consisting of peptide 74A (SEQ ID NO: 1); peptide 165 (SEQ ID NO: 2); an immunogenic fragment of peptide 74A or peptide 165, wherein the immunogenic fragment maintains the function of peptide 74A or peptide 165 as a CD8 T cell epitope of the vaccinia or variola virus; an immunogenic mutant of peptide 74A or peptide 165, wherein the immunogenic mutant maintains the function of peptide 74A or peptide 165 as a CD8 T cell epitope of the vaccinia or variola virus, is the same length as peptide 74A or peptide 165, and 1 to 4 amino acids of peptide 74A or peptide 165 are substituted in the immunogenic mutant; and a combination thereof; wherein if the individual's T cells become activated in the presence of the peptide, then the individual has been infected with the vaccinia or variola virus.

7. The method of claim 6 wherein the individual's T cells are present in a sample, and the sample is selected from the group consisting of blood, lymph and tissue.

8. The method of claim 7 wherein the sample is a peripheral blood mononuclear cell sample.

9. The method of claim 6 wherein the whether the individual's T cells become activated is determined using an assay selected from the group consisting of a cytokine assay, a flow cytometry assay and a limiting dilution assay.

10. The method of claim 9 wherein the cytokine assay is an ELISPOT assay and the flow cytometry assay is a tetramer staining assay.

11. A method of identifying T cells in a sample that become activated in the presence of a vaccinia or variola virus that comprises a polypeptide having an amino acid sequence that is identical or substantially homologous to peptide 74A (SEQ ID NO: 1), comprising contacting the T cells with a peptide selected from the group consisting of peptide 74A (SEQ ID NO: 1); an immunogenic mutant or fragment of peptide 74A, wherein the immunogenic fragment maintains the function of peptide 74A as a CD8 T cell epitope of the vaccinia or variola virus an immunogenic mutant of peptide 74A, wherein the immunogenic mutant maintains the function of peptide 74A as a CD8 T cell epitope of the vaccinia or variola virus, is the same length as peptide 74A, and 1 to 4 amino acids of peptide 74A are substituted in the immunogenic mutant; and a combination thereof; wherein activation of the T cells by the peptide indicates that the T cells become activated in the presence of the vaccinia or variola virus.

12. A method of determining whether an individual has been infected with a vaccinia or variola virus that comprises a polypeptide having an amino acid sequence that is identical or substantially homologous to peptide 74A (SEQ ID NO: 1), comprising determining whether the T cells in a sample from the individual become activated in the presence of a peptide selected from the group consisting of peptide 74A (SEQ ID 1); an immunogenic fragment of peptide 74A, wherein the immunogenic fragment maintains the function of peptide 74A as a CD8 T cell epitope of the vaccinia or variola virus; an immunogenic mutant of peptide 74A, wherein the immunogenic mutant maintains the function of peptide 74A as a CD8 T cell epitope of the vaccinia or variola virus, is the same length as peptide 74A and 1 to 4 amino acids of peptide 74A are substituted in the immunogenic mutant; and a combination thereof; wherein if the individual's T cells become activated in the presence of the peptide, then the individual has been infected with the vaccinia or variola virus.

* * * * *

UNITED STATES PATENT AND TRADEMARK OFFICE
CERTIFICATE OF CORRECTION

PATENT NO. : 7,803,566 B2
APPLICATION NO. : 11/731784
DATED : September 28, 2010
INVENTOR(S) : Masanori Terajima, John Cruz and Francis A. Ennis It is certified that error appears in the above-identified patent and that said Letters Patent is hereby corrected as shown below:

On the face of the patent in the References Cited Field (56) under Foreign Patent Documents, delete "WO 9/515764" and insert --WO 95/15764--.

On the face of the patent in the References Cited Field (56) under Foreign Patent Documents, delete "WO 9/803192" and insert --WO 98/03192--.

In Claim 9, Column 26, Line 64, delete the second occurrence of "whether the".

In Claim 11, Column 27, Line 10, delete "mutant or".

Signed and Sealed this
First Day of February, 2011

David J. Kappos
*Director of the United States Patent and Trademark Office*